(12) United States Patent
Bischoff et al.

(10) Patent No.: US 10,215,726 B2
(45) Date of Patent: Feb. 26, 2019

(54) SENSOR ELEMENT FOR DETECTING AT LEAST ONE PROPERTY OF A MEASURED GAS IN A MEASURED GAS CHAMBER, AND METHOD FOR MANUFACTURING THE SAME

(71) Applicant: Robert Bosch GmbH, Stuttgart (DE)

(72) Inventors: Alexander Bischoff, Eberdingen (DE); Andreas Rottmann, Stettfeld (DE); Antje Taeuber, Hirschaid (DE); Frank Buse, Stuttgart (DE); Jens Schneider, Leonberg (DE); Oliver Dotterweich, Oberhaid (DE); Peter Alt, Frensdorf (DE); Thomas Juestel, Hirschaid-Juliushof (DE)

(73) Assignee: ROBERT BOSCH GMBH, Stuttgart (DE)

( * ) Notice: Subject to any disclaimer, the term of this patent is extended or adjusted under 35 U.S.C. 154(b) by 250 days.

(21) Appl. No.: 15/302,392

(22) PCT Filed: Feb. 20, 2015

(86) PCT No.: PCT/EP2015/053565
§ 371 (c)(1),
(2) Date: Oct. 6, 2016

(87) PCT Pub. No.: WO2015/154905
PCT Pub. Date: Oct. 15, 2015

(65) Prior Publication Data
US 2017/0030858 A1     Feb. 2, 2017

(30) Foreign Application Priority Data

Apr. 10, 2014    (DE) ........................ 10 2014 206 958

(51) Int. Cl.
*G01N 27/407* (2006.01)
*H05K 3/42* (2006.01)
(Continued)

(52) U.S. Cl.
CPC ........... *G01N 27/4075* (2013.01); *G01K 7/26* (2013.01); *G01K 13/02* (2013.01);
(Continued)

(58) Field of Classification Search
CPC ............... G01N 27/406; G01N 27/407; G01N 27/4071; G01N 27/409; G01N 27/41;
(Continued)

(56) References Cited

U.S. PATENT DOCUMENTS 5,142,266 A    8/1992   Friese et al.
7,084,350 B2    8/2006   De La Prieta et al.
(Continued)

FOREIGN PATENT DOCUMENTS

CN     102066915 A    5/2011
EP      2058650 A1    5/2009
(Continued)

OTHER PUBLICATIONS

International Search Report dated May 29, 2015, of the corresponding International Application PCT/EP2015/053565, filed Feb. 20, 2015.
(Continued)

*Primary Examiner* — Alexander S Noguerola
(74) *Attorney, Agent, or Firm* — Norton Rose Fulbright US LLP; Gerard Messina

(57) ABSTRACT

A sensor element for detecting a level of a gas component in the measured gas or a temperature of the measured gas. The sensor element includes at least one solid electrolyte layer. The solid electrolyte layer has at least one plated-through hole. The sensor element further includes a conductive
(Continued)

element, which produces an electrically conductive connection through the plated-through hole. In the plated-through hole, the solid electrolyte layer is electrically insulated from the conductive element by an insulating element. At least one opening region of the plated-through hole is stabilized against phase transition by a stabilizing element. The stabilizing element is made at least partially of a material, which includes a noble metal and an element selected from the group consisting of: V, Nb, Ta, Sb, Bi, Cr, Mo, W. A method for manufacturing the sensor element is also provided.

13 Claims, 3 Drawing Sheets

(51) Int. Cl.
*G01K 7/26* (2006.01)
*G01K 13/02* (2006.01)
*G01N 27/406* (2006.01)
*H05K 3/40* (2006.01)

(52) U.S. Cl.
CPC ..... *G01N 27/4062* (2013.01); *G01N 27/4071* (2013.01); *G01N 27/4073* (2013.01); *H05K 3/42* (2013.01); *G01K 2013/024* (2013.01); *H05K 3/4061* (2013.01)

(58) Field of Classification Search
CPC ..... F02D 2200/0804; F02D 2009/0222; F02D 2041/0067; F02D 41/1446
See application file for complete search history.

(56) References Cited

U.S. PATENT DOCUMENTS

2010/0038120 A1* 2/2010 Kojima ............... H01G 4/232
  174/257
2011/0162436 A1 7/2011 Wahl et al.

FOREIGN PATENT DOCUMENTS

| JP | S61134655 A | 6/1986 |
| JP | H05507988 A | 11/1993 |
| WO | 03102569 A1 | 12/2003 |

OTHER PUBLICATIONS

Konrad Reif (ed.), "Sensors in the Motor Vehicle", 1st edition, 2010, pp. 160-165 (english translation).

* cited by examiner

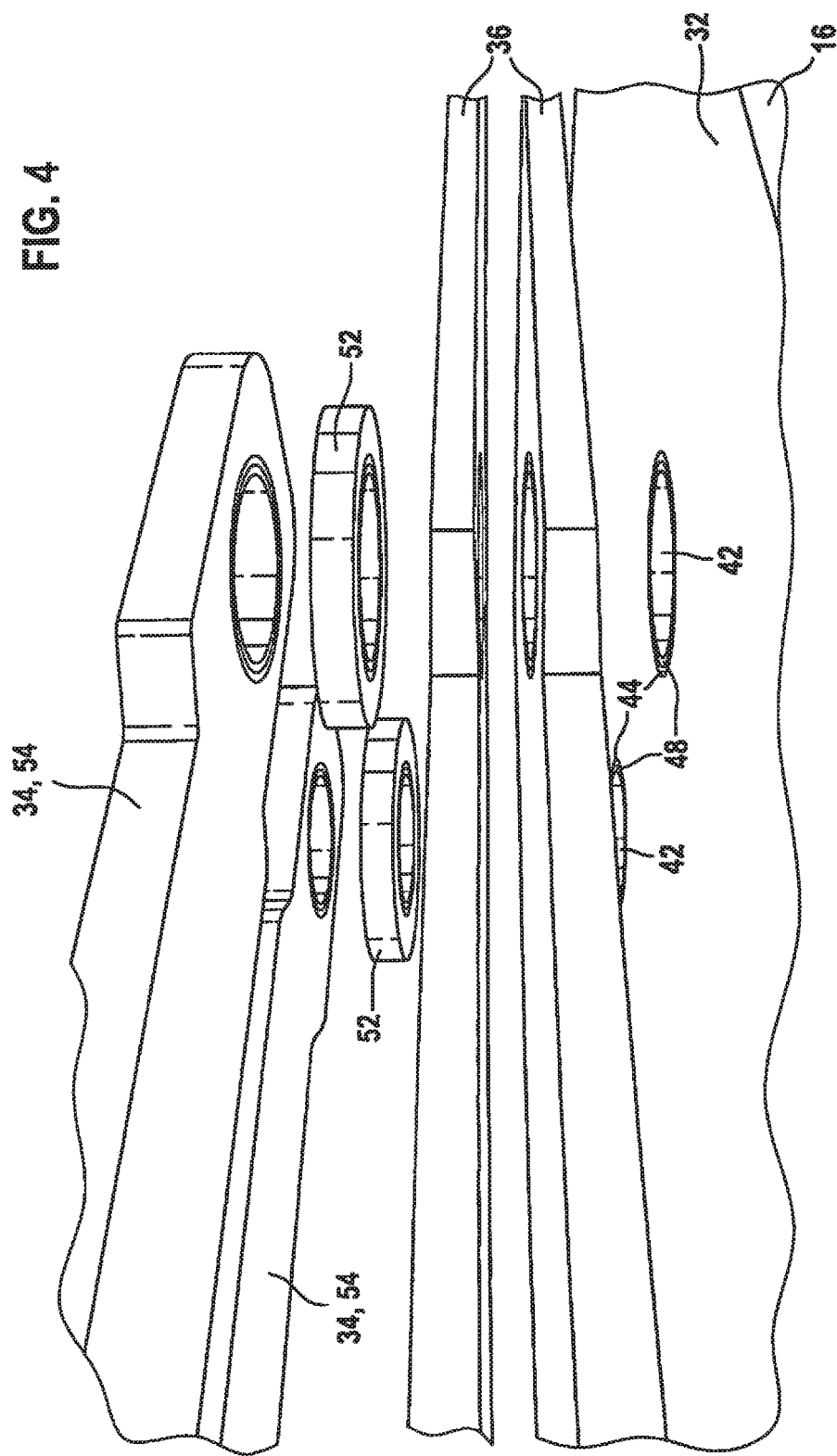

SENSOR ELEMENT FOR DETECTING AT LEAST ONE PROPERTY OF A MEASURED GAS IN A MEASURED GAS CHAMBER, AND METHOD FOR MANUFACTURING THE SAME

BACKGROUND INFORMATION

There are a multitude of sensor elements and methods for detecting at least one property of a measured gas in a measured gas chamber in the related art. In this context, it may be, in general, any physical and/or chemical property, one or more properties being able to be measured. In the following, the present invention is described, in particular, with reference to a qualitative and/or quantitative determination of a level of a gas component of the measured gas, in particular, with reference to a determination of an oxygen concentration in the measured gas. The oxygen concentration may be measured, for example, in the form of a partial pressure and/or in the form of a percentage. However, alternatively or in addition, other properties of the measured gas, such as the temperature, are also measurable.

For example, such sensor elements may take the form of so-called oxygen sensors, as are known from, e.g., Konrad Reif (ed.): Sensors in the Motor Vehicle, 1st ed., 2010, pages 160-165. Using broadband oxygen sensors, in particular, planar broadband oxygen sensors, e.g., the oxygen concentration in the exhaust gas may be determined in a large range, and therefore, the air-fuel ratio in the combustion chamber may be inferred. The excess-air factor describes this air-fuel ratio.

The related art describes, in particular, ceramic sensor elements, which are based on the use of electrolytic properties of specific solids, and thus, on ion-conducting properties of these solids. In particular, these solids may be ceramic solid electrolytes, such as zirconium dioxide ($ZrO_2$), especially, yttrium-stabilized zirconium dioxide (YSZ) and scandium-doped zirconium dioxide (ScSZ), which may include small additions of aluminum oxide ($Al_2O_3$) and/or silicon dioxide ($SiO_2$). Thus, in the case of such sensor elements, e.g., a laminated construction of ceramic substrates having inner heating-element and electrode structures is known, which are connected to a voltage source and/or evaluation unit via a plated-through hole.

In spite of the numerous advantages of the conventional sensor elements, they still have potential for improvement. Increasing functional demands are being placed on such sensor elements. Different and sometimes mutually opposing requirements must be satisfied for a robust and reliable design of the plated-through holes. Thus, there must be a high electrical resistance between the plated-through holes, even at operating temperatures above 500° C. This may realized, for example, by an insulating layer of electrically insulating material, such as aluminum oxide. The basic mechanical strength of the YSZ carrier body ceramic may only be reduced slightly by the introduction of several plated-through holes. This may be achieved by small diameters and smooth, crack-free walls of the plated-through holes. The plated-through holes should be produced by stable and inexpensive manufacturing processes usable in the case of multiple printed circuits. This may be achieved, for example, using multiple stamping, boring or stack suction. In addition, breakup of the YSZ carrier ceramic by hydrothermal aging over the lifetime of the sensor element must be prevented. Hydrothermal aging involves, in particular, a phase transition of the zirconium dioxide from the tetragonal phase to the monoclinic phase, which may produce a mechanical breakup or even a rupture of the weakened ceramic in response to vibration or shocks. The phase transition may begin, in particular, in the region of the stamping burr, thin through-hole plating, a niobium-free terminal contact paste, and missing insulation.

SUMMARY

Thus, a sensor element for detecting at least one property of a measured gas in a measured gas chamber and a method for manufacturing the same are provided, which at least substantially may eliminate the disadvantages of conventional sensor elements, and in the case of which, in particular, an increased stability against breakup through phase transition is present.

A sensor element of the present invention for detecting at least one property of a measured gas in a measured gas chamber, in particular, for detecting a level of a gas component in the measured gas or a temperature of the measured gas, includes at least one solid electrolyte layer, the solid electrolyte layer having at least one plated-through hole; and a conductive element, which produces an electrically conductive connection through the plated-through hole, from an upper side of the solid electrolyte layer to a lower side of the solid electrolyte layer. In the plated-through hole, the solid electrolyte layer is electrically insulated from the conductive element by an insulating element. At least one opening region of the plated-through hole is stabilized against phase transition by a stabilizing element. The stabilizing element is made at least partially of a material, which includes a noble metal and an element selected from the group consisting of V, Nb, Ta, Sb, Bi, Cr, Mo, W.

The noble metal may be platinum. A level of the element in the material may be from 2% by weight to 10% by weight. The element may be present in the form of at least one compound selected from the group consisting of oxide, oxychloride, carbonate, carbide and chloride. The stabilizing element may surround the opening region completely in a circumferential direction. For example, the stabilizing element surrounds the opening region annularly. The insulating element may be made at least partially of a material, which is an oxidic dielectric. The dielectric is, for example, a metallic oxide or an alkaline earth metal spinel.

A method of the present invention for manufacturing a sensor element for detecting at least one property of a measured gas in a measured gas chamber, in particular, for detecting a level of a gas component in the measured gas or a temperature of the measured gas, includes the following steps, preferably in the indicated order:

providing at least one solid electrolyte layer;
introducing at least one plated-through hole into the solid electrolyte layer, which extends from an upper side of the solid electrolyte layer to a lower side of the solid electrolyte layer;
introducing an insulating paste into the plated-through hole;
introducing a conductive paste into the plated-through hole;
depositing a stabilizing paste against phase transition onto at least one opening region of the plated-through hole, the stabilizing paste including a material, which has a noble metal and an element selected from the group consisting of V, Nb, Ta, Sb, Bi, Cr, Mo, W; and
sintering the sensor element with the insulating paste, the conductive paste and/or the stabilizing paste.

The noble metal may be platinum. A level of the element in the material may be from 2% by weight to 10% by weight.

The element may be present in the form of at least one compound selected from the group consisting of oxide, oxychloride, carbonate, carbide and chloride.

The method as recited in one of the four preceding claims, the stabilizing paste being deposited in such a manner, that it surrounds the opening region completely in a circumferential direction. The stabilizing paste may be deposited so that it surrounds the opening region annularly. The insulating paste may include a material that is an oxidic dielectric. The dielectric may be a metallic oxide or an alkaline earth metal spinel. The stabilizing paste may be deposited in layers. The stabilizing paste may be deposited prior to introducing the insulating paste, the insulating paste being introduced prior to introducing the conductive paste. The stabilizing paste may be deposited, using a printing method. The insulating paste and/or the conductive paste may be introduced, using at least one vacuum suction method, or using at least one suitable printing method.

In the scope of the present invention, a solid electrolyte layer is to be understood as a layered body or object having electrolytic properties, thus, ion-conducting properties. In particular, it may be a ceramic solid electrolyte layer.

This also includes the raw material of a solid electrolyte layer, and therefore, the form of a so-called green compact or brown compact, which first becomes a solid electrolyte after sintering.

In the scope of the present invention, a layer is to be understood as a planar extension of a uniform material of a certain height, which may be situated between, above, below or on other elements.

In the scope of the present invention, an insulating element is to be understood as a body or object having electrically insulating properties. Analogously, an insulating paste is to be understood as a material, which is in the form of a paste and forms an insulating element after a treatment step, in particular, a thermal treatment step such as sintering.

In the scope of the present invention, a conductive element is to be understood as a body or object having electrically conductive properties. Analogously, a conductive paste is to be understood as a material, which is in the form of a paste and forms a conductive element after a treatment step, in particular, a thermal treatment step such as sintering.

In the scope of the present invention, a stabilizing element is to be understood as a body or object having stabilizing properties against breakup by hydrothermal aging, which can result in phase transition. Analogously, a stabilizing paste is to be understood as a material, which is in the form of a paste and forms a stabilizing element after a treatment step, in particular, a thermal treatment step such as sintering.

In the scope of the present invention, a phase of a material is to be understood as the characteristic of the material of occurring in different states. Thus, the material has the same chemical composition (stoichiometry), but differs in the spatial arrangement of the atoms and has different properties.

In the scope of the present invention, a phase transition is to be understood as a transition of a material from one phase into another. Consequently, the transition may produce different structures of the material. The phase transition is produced by influences, such as pressure and/or temperature. Thus, zirconium dioxide occurs in several phases, for example. Below a temperature of 1173° C., zirconium dioxide exists in the monoclinic phase, above it, in the tetragonal phase, and above 2370° C., in the cubic phase. Above 2690° C., zirconium dioxide exists as a molten mass.

BRIEF DESCRIPTION OF THE DRAWINGS

Further optional details and features of the present invention become apparent from the following description of preferred exemplary embodiments, which are schematically represented in the figures.

FIG. 4 shows an exploded view of a part of the sensor element.

DETAILED DESCRIPTION OF EXAMPLE EMBODIMENTS

Figure 1:
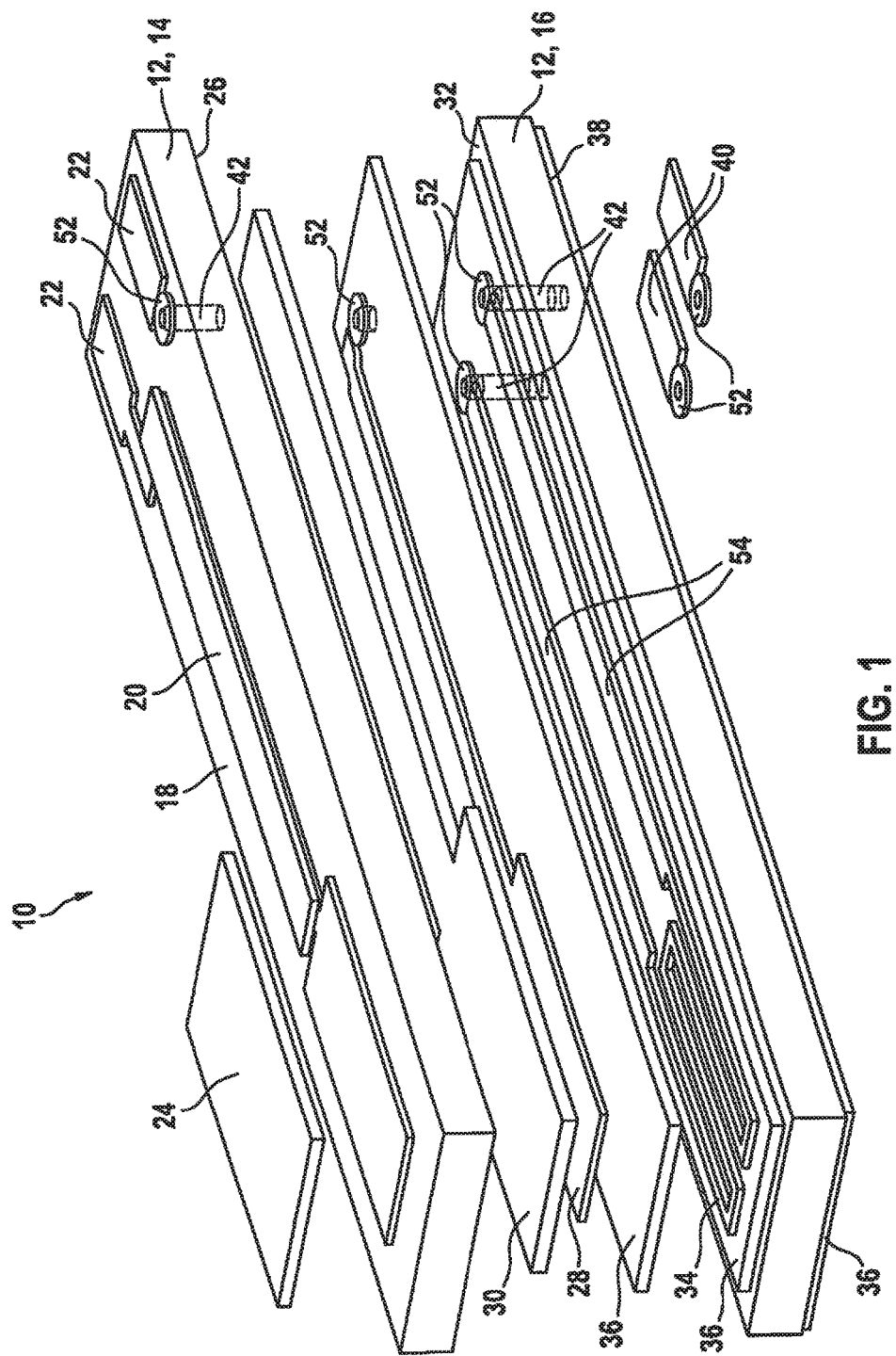
FIG. 1 shows an exploded view of a sensor element according to the present invention.

FIG. 1 shows an exploded view of a sensor element 10 according to a specific embodiment of the present invention. The sensor element 10 represented in FIG. 1 may be used for detecting physical and/or chemical properties of a measured gas, one or more properties being able to be measured. In the following, the present invention is described, in particular, with reference to a qualitative and/or quantitative determination of a gas component of the gas, in particular, with reference to a determination of an oxygen concentration in the measured gas. The oxygen concentration may be measured, for example, in the form of a partial pressure and/or in the form of a percentage. However, in general, other types of gas components are also detectable, such as nitrogen oxides, hydrocarbons, soot particles and/or hydrogen. However, alternatively or in addition, other properties of the measured gas, such as the temperature, are also measurable. The present invention is applicable, in particular, in the area of automotive technology, so that the measured gas chamber may be, in particular, an exhaust tract of an internal combustion engine, and the measured gas may be, in particular, an exhaust gas.

In a correspondingly exemplary manner, sensor element 10 may be part of a planar oxygen sensor and has at least one solid electrolyte layer 12. Solid electrolyte layer 12 may be, in particular, a ceramic solid electrolyte layer 12, such as zirconium dioxide, in particular, yttrium-stabilized zirconium dioxide and scandium-doped zirconium dioxide, which may include small additions of aluminum oxide and/or silicon oxide. In a merely exemplary manner, a first solid electrolyte layer 14 and a second solid electrolyte layer 16 are provided. First solid electrolyte layer 14 and second solid electrolyte layer 16 each have a layer thickness of 150 µm to 850 µm, for example, 500 µm. An outer electrode 20 and terminal contacts 22 are situated on an upper side 18 of first solid electrolyte layer 14. Outer electrode 20 may be at least partially covered by a porous protective layer 24. An inner electrode 28, which may be used as a reference electrode, is situated in a reference gas channel 30, on a lower side 26 of first solid electrolyte layer 14.

Second solid electrolyte layer 16 is situated beneath first solid electrolyte layer 14. A heating element 34, which is embedded between two insulating layers 36, is situated on an upper side 32 of second solid electrolyte layer 16. Terminal contacts 40 are situated on a lower side 38 of second solid electrolyte layer 16.

Altogether, as described below in more detail, several plated-through holes 42 are provided in sensor element 10, adjacent to terminal contacts 22, 40, for electrically contacting inner electrodes 28 and heating element 34. More precisely, first solid electrolyte layer 14 has one plated-through hole 42, and second solid electrolyte layer 16 has two plated-through holes 42. Plated-through holes 42 may take the form of boreholes and/or punched holes. Plated-through holes 42 each have a diameter of 400 μm to 1000 μm, for example, 600 μm. Since plated-through holes 42 are used for electrically contacting electrical components, it is apparent that the number of plated-through holes 42 is a function of the number of components to be contacted.

Accordingly, more or fewer plated-through holes 42 than described above may be provided as a function of the number of components to be contacted. Plated-through holes 42 extend completely through, that is, penetrate first solid electrolyte layer 14 and second solid electrolyte layer 16. In other words, plated-through hole 42 of first solid electrolyte layer 14 extends from upper side 18 to lower side 26, or vice versa, and plated-through holes 42 of second solid electrolyte layer 16 extend from upper side 32 to lower side 38. In a merely exemplary manner, the construction of sensor element 10 in the region of a plated-through hole 42 is described below in view of second solid electrolyte layer 16. The construction of sensor element 10 in the region of a plated-through hole 42 of first solid electrolyte layer 16 is generally identical, so that in the following, commonalities between first solid electrolyte layer 14 and second solid electrolyte layer 16 are not discussed, but only the differences.

Figure 2:
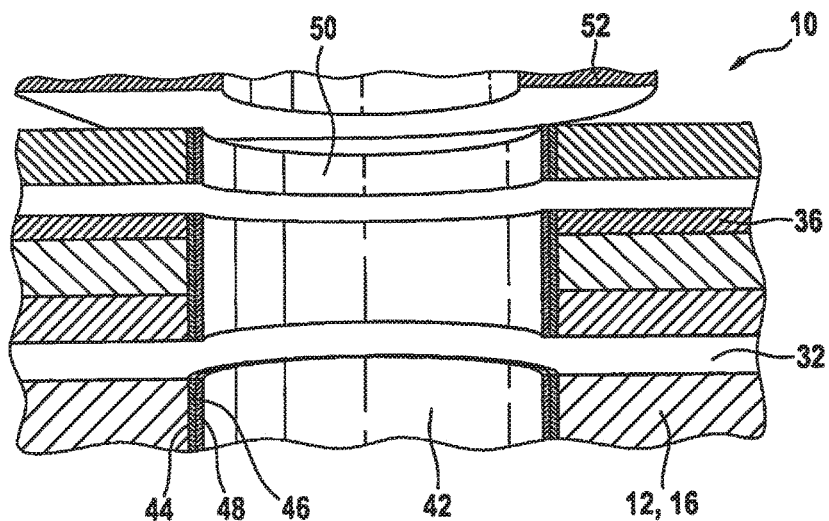
FIG. 2 shows a partial cross-sectional view of the sensor element in the region of a plated-through hole.

FIG. 2 shows a partial cross-sectional view of sensor element 10 in the region of a plated-through hole. More precisely, a partial cross-section of second solid electrolyte layer 16 is represented in FIG. 2. Insulating layer 36 is situated on upper side 32. Although not represented in further detail in FIG. 2, an insulating layer 36 may also be situated on lower side 38 of second solid electrolyte layer 16. In this context, plated-through hole 42 extends from upper side 32 to lower side 38. In so doing, plated-through hole 42 also penetrates insulating layers 36. A layered insulating element 44 is situated in the interior of plated-through hole 42. Layered insulation element 44 has a layer thickness of 5 μm to 40 μm, for example, 20 μm. Insulating element 44 is made of at least one electrically insulating material. In particular, insulating element 44 is made at least partially of a material, which is an oxidic dielectric. The dielectric may be a metallic oxide or an alkaline earth metal spinel. The electrically insulating material includes, for example, aluminum oxide ($Al_2O_3$). Insulating element 44 covers a wall 46 of plated-through hole 42 completely. Consequently, insulating element 44 also covers wall 46 of plated-through hole 42 in the region of insulating layer 36.

A conductive element 48 is situated on insulating element 44. Conductive element 48 is also layered. Layered conductive element 48 has a layer thickness of 5 μm to 15 μm, for example, 10 μm. Conductive element 48 is made of an electrically conductive material. The electrically conductive material includes, for example, a noble metal, in particular, platinum. The electrically conductive material may include further additives, such as niobium oxide. In this context, conductive element 48 covers insulating element 44 completely. Due to this construction, conductive element 48 establishes an electrically conductive connection through plated-through hole 42, from upper side 32 of second solid electrolyte layer 16 to lower side 38 of second solid electrolyte layer 16. In addition, in plated-through hole 42, second solid electrolyte layer 16 is electrically insulated from conductive element 48 by insulating element 44.

An opening region 50 of plated-through hole 42 is stabilized against phase transition by a stabilizing element 52. Stabilizing element 52 is made of a material that includes a noble metal and an element selected from the group consisting of V, Nb, Ta, Sb, Bi, Cr, Mo, W. For example, the noble metal is platinum. The element may be present in the form of at least one compound, which is selected from the group consisting of oxide, oxychloride, carbonate, carbide and chloride. A level of the element in the material of stabilizing element 52 is always from 2% by weight to 10% by weight, for example, 5% by weight. The element is Nb, for example, and is present as a compound in the form of niobium oxide. Consequently, the material of stabilizing element 52 includes, inter alia, platinum and niobium oxide. Stabilizing element 52 is also layered. Layered stabilizing element 52 has a layer thickness of 7 μm to 11 μm, for example, 9 μm. Stabilizing element 52 surrounds opening region 50 completely in a circumferential direction. For example, stabilizing element 52 is positioned in such a manner, that it surrounds opening region 50 annularly. Opening region 50 may be understood as a mouth region of plated-through hole 42, which means that stabilizing element 52 also extends partially into plated-through hole 42.

Figure 3:
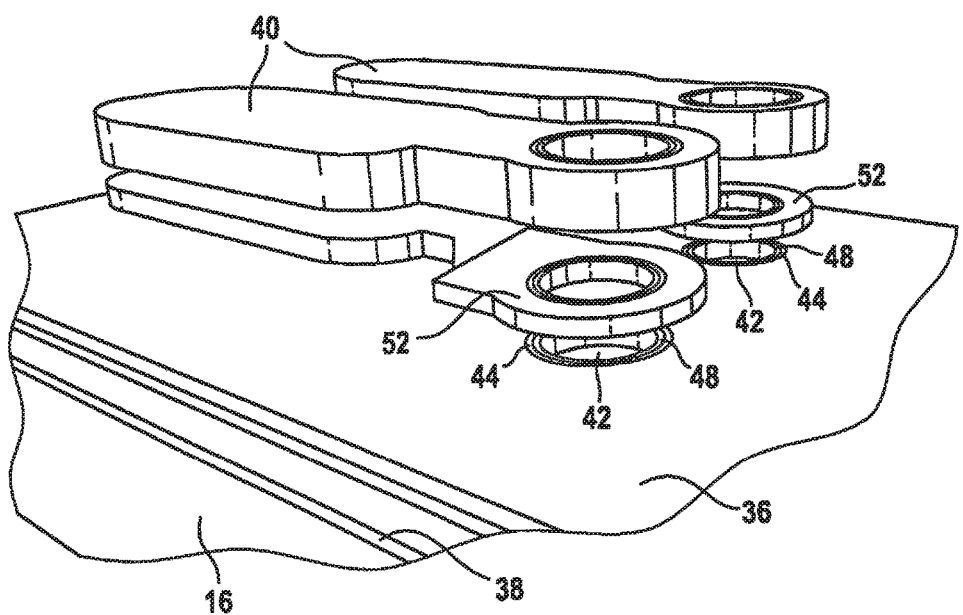
FIG. 3 shows a view from below of a part of the sensor element.

FIG. 3 shows a view from below of a part of sensor element 10. More precisely, lower side 38 of second solid electrolyte layer 16 is represented in FIG. 3. As can be seen in FIG. 3, an insulating layer 36 is also situated on lower side 38. In addition, the annular construction of stabilizing elements 52 in, in each instance, the opening region 50 of each plated-through hole 42, is apparent. In this context, each stabilizing element 52 contacts a terminal contact 40 electrically.

FIG. 4 shows a partially exploded view of sensor element 10. More precisely, upper side 32 of second solid electrolyte layer 16 is represented in FIG. 4. As can be seen in FIG. 4, insulating layer 36 is also situated on upper side 32. In addition, the annular construction of stabilizing elements 52 in, in each instance, the opening region 50 of each plated-through hole 42, is apparent. In each instance, a stabilizing element 52 electrically contacts a supply lead track 54 of heating element 34.

Second solid electrolyte layer 16 is electrically insulated from conductive element 48 by insulating element 44. However, due to stabilizing element 52 and conductive element 48, electrical contacting is produced through plated-through hole 42, from terminal contact 40 to heating element 34.

The construction of sensor element 10 in the region of plated-through hole 42 of first solid electrolyte layer 14 only differs from the construction of sensor element 10 in the region of plated-through hole 42 of second solid electrolyte layer 16 in that, in the case of first solid electrolyte layer 14, no insulating layers 36 are provided. Consequently, in the case of first solid electrolyte layer 14, electrical contacting is analogously produced through plated-through hole 42, from terminal contact 22 to inner electrode 28. The design of plated-through hole 42 of the present invention to have insulating element 44, conductive element 48 and stabilizing element 52 produces a greater insulation resistance between terminal contacts 22, 40, even at high temperatures such as a resistance of 100 kΩ at a temperature of 500° C., and simultaneously produces reliable resilience against breakup through phase transition in the middle temperature range of 100° C. to 400° C., in the presence of moisture and/or water.

Sensor element 10 may be manufactured as follows. In this context, the method is described in a merely exemplary manner, in view of the construction in the case of second solid electrolyte layer 16. In the case of first solid electrolyte layer 14, the method is identical with the exception of the above-described differences.

Solid electrolyte layer 16 is initially provided. Second solid electrolyte layer 16 is provided in an unsintered state. Insulating layers 36 are deposited onto upper side 32 and lower side 34. For example, insulating layers 36 are laminated as films onto upper side 32 and lower side 34. Plated-through holes 42 are introduced into second solid electrolyte layer 14. In this context, plated-through holes 42 are introduced in such a manner, that plated-through holes 42 extend from upper side 32 to lower side 38 of second solid electrolyte layer 16, as well as through insulating layers 36. The introduction may be carried out, for example, by punching, stamping and/or one- or two-sided boring, in particular, with the aid of laser radiation.

Subsequently, an insulating paste is introduced one or more times into plated-through holes 42. The paste may also be in the form of a suspension. In particular, the insulating paste is made at least partially of a material, which is an oxidic dielectric. The dielectric may be a metallic oxide or an alkaline earth metal spinel. The electrically insulating material includes, for example, aluminum oxide ($Al_2O_3$). The introduction may be accomplished, for example, by printing, silk-screen printing, one- or two-sided suction, pressing, spray-on deposition and/or dripping. For example, the insulating paste is introduced by a vacuum suction method. The insulating paste is introduced, in particular, in layers having a layer thickness of 5 µm to 40 µm. Finally, and in the case of repeated introduction, drying may also be carried out in the interim.

Subsequently, a conductive paste is introduced one or more times into plated-through holes 42. The conductive paste is made of an electrically conductive material. The electrically conductive material includes, for example, a noble metal, in particular, platinum. The electrically conductive material may include further additives, such as niobium oxide. The introduction may be carried out, for example, by printing, silk-screen printing, one- or two-sided suction, pressing, spray-on deposition and/or dripping. For example, the insulating paste is introduced by a vacuum suction method. The insulating paste is introduced, in particular, in layers having a layer thickness of 5 µm to 15 µm. Finally, and in the case of repeated introduction, drying may also be carried out in the interim.

Subsequently, a stabilizing paste against phase transition is deposited onto opening region 50. The stabilizing paste may contain a material, which includes a noble metal, such as platinum, and an element that is selected from the group consisting of V, Nb, Ta, Sb, Bi, Cr, Mo, W. The element may be present in the form of at least one compound, which is selected from the group consisting of oxide, oxychloride, carbonate, carbide and chloride. A level of the element in the material of the stabilizing paste is always from 2% by weight to 10% by weight, for example, 5% by weight. The element is Nb, for example, and is present as a compound in the form of niobium oxide. Consequently, the material of the stabilizing paste includes, inter alia, platinum and niobium oxide. The stabilizing paste may be deposited, using a printing method. For example, the stabilizing paste is imprinted in layers. The stabilizing paste is deposited, in particular, in layers having a layer thickness of 5 µm to 15 µm. In this context, the stabilizing paste may be deposited annularly about opening region 50.

An exact summary of the contents of the insulating paste, the conductive paste and the stabilizing paste may be as follows:

A. Insulating Paste

| Raw material | Percent by weight |
| --- | --- |
| Plasticizer | 2.0-5.0% |
| Solvent | 25-45% |
| Binder polymer | 5.0-10% |
| $Al_2O_3$ or spinel powder | 40-60% |
| Lampblack | 2.0-6.0% |

B. Conductive Paste

| Raw material | Percent by weight |
| --- | --- |
| Solvent + binder | 25-45% |
| Pt powder | 45-70% |
| Pd powder/resinate | 0-5% |
| Rh powder/resinate | 0-5% |
| Zirconium mixed oxide | 2-10% |

C. Stabilizing Paste

| Raw material | Percent by weight |
| --- | --- |
| Solvent + binder | 25-45% |
| M(V)/M(VI) compound | 2-12% |
| Pt powder | 40-65% |
| Pd powder/resinate | 0-5% |
| Rh powder/resinate | 0-5% |
| Stabilized $ZrO_2$ | 0-10% |

In the present exemplary embodiment, the recipes of the conductive paste and stabilizing paste are very similar. This is not absolutely necessary, however. Crucial is the level of at least 2.0% by weight of a metallic compound having a metal of oxidation number +V or +VI for counterdoping the metallic ions having a metal of oxidation number +II or +III in the phase-stabilized zirconium dioxide of the ceramic of second solid electrolyte layer 16. This applies correspondingly to first solid electrolyte layer 14.

What finally follows then, is a sintering process of sensor element 10 with all of the deposited pastes and all of the solid electrolyte layers 12, 14, 16 positioned on top of one another. The sintering may take place, for example, at a temperature of 1350° C. to 1450° C. In this context, solid electrolyte layers 12, 14, 16, insulating layers 36, the insulating paste, the conductive paste and the stabilizing paste are cosintered. Through the sintering process, insulating element 44, conductive element 48 and stabilizing element 52 are formed from the insulating paste, the conductive paste and the stabilizing paste.

What is claimed is:

1. A sensor element for detecting a level of a gas component in a measured gas or a temperature of the measured gas, the sensor element comprising:
    at least one solid electrolyte layer, the solid electrolyte layer having at least one plated-through hole; and
    a conductive element which produces an electrically conductive connection through the plated-through hole, from an upper side of the solid electrolyte layer to a lower side of the solid electrolyte layer, wherein in the plated-through hole, the solid electrolyte layer is electrically insulated from the conductive element by an insulating element;

wherein at least one opening region of the plated-through hole is stabilized against phase transition by a stabilizing element, the stabilizing element being made at least partially of a material, which includes a noble metal and an element selected from the group consisting of V, Nb, Ta, Sb, Bi, Cr, Mo, and W, and wherein the stabilizing element surrounds the opening region one of: (i) completely in a circumferential direction, or (ii) annularly.

2. The sensor element as recited in claim 1, wherein the noble metal is platinum.

3. The sensor element as recited in claim 1, wherein a level of the element in the material is from 2% by weight to 10% by weight.

4. The sensor element as recited in claim 1, wherein the element is present in the form of at least one compound selected from the group consisting of oxide, oxychloride, carbonate, carbide and chloride.

5. The sensor element as recited in claim 1, wherein the stabilizing element surrounds the opening region completely in the circumferential direction.

6. The sensor element as recited in claim 1, wherein the stabilizing element surrounds the opening region annularly.

7. The sensor element as recited in claim 1, wherein the insulating element is made at least partially of a material, which is an oxidic dielectric.

8. A method for manufacturing a sensor element for detecting a level of a gas component in the measured gas or a temperature of the measured gas, comprising:

providing at least one solid electrolyte layer;

introducing at least one plated-through hole into the solid electrolyte layer, the plated-through hole extending from an upper side of the solid electrolyte layer to a lower side of the solid electrolyte layer;

introducing an insulating paste into the plated-through hole;

introducing a conductive paste into the plated-through hole;

depositing a stabilizing paste against phase transition onto at least one opening region of the plated-through hole, the stabilizing paste including a material, which has a noble metal and an element selected from the group consisting of V, Nb, Ta, Sb, Bi, Cr, Mo, and W; and sintering the sensor element with at least one of the insulating paste, the conductive paste, and the stabilizing paste;

wherein the stabilizing paste is deposited so that it surrounds the opening region annularly.

9. The method as recited in claim 8, wherein a level of the element in the material is from 2% by weight to 10% by weight.

10. The method as recited in claim 8, wherein the element is present in the form of at least one compound selected from the group consisting of oxide, oxychloride, carbonate, carbide and chloride.

11. The method as recited in claim 8, wherein the stabilizing paste is deposited prior to introducing the insulating paste, and the insulating paste is introduced prior to introducing the conductive paste.

12. The method as recited in claim 8, wherein the stabilizing paste is deposited using a printing method.

13. The method as recited in claim 8, wherein at least one of the insulating paste and the conductive paste is introduced using at least one vacuum suction method.

* * * * *